United States Patent [19]

Hagiwara et al.

[11] Patent Number: 5,407,696
[45] Date of Patent: Apr. 18, 1995

[54] GREEN JUICES OR DRY POWDERS THEREOF

[75] Inventors: Yoshihide Hagiwara, 4-14, Hiraisanso, Takarazuka-shi, Hyogo 665; Hideaki Hagiwara, Takarazuka, both of Japan

[73] Assignee: Yoshihide Hagiwara, Takarazuka, Japan

[21] Appl. No.: 983,846

[22] PCT Filed: Jul. 2, 1992

[86] PCT No.: PCT/JP92/00832
§ 371 Date: Mar. 2, 1993
§ 102(e) Date: Mar. 2, 1993

[87] PCT Pub. No.: WO93/00831
PCT Pub. Date: Jan. 21, 1993

[30] Foreign Application Priority Data

Jul. 3, 1991 [JP] Japan .................................. 3-188232

[51] Int. Cl.$^6$ ......................... A23K 3/02; A23L 1/025
[52] U.S. Cl. ..................................... 426/636; 426/271; 426/465; 426/489; 426/599
[58] Field of Search ............... 426/271, 636, 599, 489, 426/465

[56] References Cited

U.S. PATENT DOCUMENTS 2,465,967  3/1949  Graham et al. ...................... 426/271

FOREIGN PATENT DOCUMENTS 3728372  3/1989  Germany ............................ 426/271

Primary Examiner—Helen Pratt
Attorney, Agent, or Firm—Sherman and Shalloway

[57] ABSTRACT

A pressed juice of green leaves of true grasses or its dry powder wherein the total amount of chlorine (Cl) and nitrate group ($NO_3$) is not more than 9% by weight based on the solids content, and a process for producing same using an ion exchange membrane or an ion exchange resin. The above pressed juice or its dry powder is substantially free from additives as a natural food, has less amounts of chlorine and nitrate group which are undesirous to a human body, is improved in palatability and preservability, and is useful in the field of food, food additives, drugs, or the like.

1 Claim, No Drawings

GREEN JUICES OR DRY POWDERS THEREOF

DETAILED DESCRIPTION OF INVENTION

This invention relates to a pressed juice of green leaves of true grasses or its dry powder, and a process for producing same. More specifically, this invention relates to a pressed juice of green leaves of true grasses or its dry powder substantially free from additives as a natural food, having less contents of chlorine and nitrate group which are undesirous to a human body and having improved palatability and preservability.

When stems and/or leaves (which are genetically named "green leaves" in the present specification) of true grasses are dried, there occurs a phenomenon that they generally fade into yellow or brown. Moreover, it is well known that even if they are kept green for a short period of time after production, dry products thereof lose a green color during storage, and changes such as browning, degradation, change in smell, etc. take place.

The present inventors have so far made studies on powdering of plant green juices obtained by pressing green leaves of true grasses, their stabilization, their long-term storing method, etc. The results thereof have been reported by the present inventors in a process for producing powders of plant green juice powder having improved drinkability (Japanese Patent Publication No. 36177/1971), a process for producing powders of cereal green leaves (Japanese Patent Publication No. 38548/1971), a process for producing powders of plant green juices (Japanese Patent Publication No. 41177/1971), and the other considerable scientific literature.

The green color of green plants is chlorophyll. It is well known that the chlorophyll is changed into pheophytin upon undergoing an action of ultraviolet rays, acids or an enzyme (chlorophyllase), and brown and red colors of pigments such as xanthophyll, carotinold, flavonoid, etc. in the green plants become prominent.

The present inventors proposed, in said Japanese Patent Publication No. 38548/1971, etc., a process in which powders of green leaves of cereals free from an offensive odor and stably preversable for a long period of time are produced by adjusting pH of a plant green juice obtained by mechanically pressing green leaves of cereals to 6 to 9 with an alkaline substance, for example, a carbonate, a bicarbonate or a hydroxide of an alkali metal or an alkaline earth metal, such as sodium carbonate, potassium carbonate, sodium bicarbonate, potassium hydroxide, ammonium hydroxide, calcium hydroxide or magnesium hydroxide, and then spray-drying or lyophilizing the resulting green juice.

The green leaf powders of cereals produced by the above proposed process can be stored for a relatively long period of time, usually 1 to 2 years without discoloration or fading of the green color inherent in the green juices. However, they contain alkaline substances added to adjust pH as stated above, which is undesirous from the aspect of a natural food in which the presence of additives is unacceptable. Moreover, the green powders usually contain about 10 to 25% by weight of minerals including the alkaline substances added to adjust pH. Half thereof are free inorganic minerals which are present in the form of inorganic acid salts (e.g., hydrochloride, nitrate, nitrite, sulfate, silicate and phosphate) of metals such as Na, K, Ca, Mg, Fe, Cu, Mn and Zn. They may ordinarily be present as composite mineral salts. These salts include a large number of salts having hygroscopicity or deliquescence which are a great cause to make wet the green leaf powders. Moreover, some of the inorganic minerals are bitter or salty, having an adverse effect on palatability of the green leaf powders.

Besides, the green leaf powder of the cereals contain considerable amounts of chlorine and nitrate group ($NO_3$) by absorption of a nitrogen fertilizer, a potassium fertilizer, etc. However, excess intake of these chlorine and nitrate group is undesirous to a human body; especially the nitrate group seems likely to be related to carcinogenesis.

The present inventors have made assiduous investigations over a process in which chlorine and nitrate group are effectively removed from a pressed juice (hereinafter referred to at times as a "green juice") obtained by mechanically pressing green leaves of true grasses by little influencing active ingredients of the pressed juice. As a result, they have found this time that the free chlorine and nitrate group in the green juice can be notably removed by using an ion exchange membrane or an ion exchange resin and a fresh green juice or its dry powder that has not existed before can thereby be obtained. This finding has led to completion of this invention.

Thus, this invention is to provide a pressed juice (green juice) of green leaves of true grasses or its dry powder (hereinafter referred to at times as a "green leaf powder" or a "green juice powder"), characterized in that the total amount of chlorine (Cl) and nitrate group ($NO_3$) is not more than 9% by weight based on the solids content.

Further, this invention is to provide a process for producing a pressed juice (green juice) of true grasses or its dry powder, which comprises electrically separating and removing free chlorine and nitrate ions at least partially from a pressed juice of green leaves of true grasses via an ion exchange membrane, and optionally drying the resulting pressed juice with said ions removed at least partially.

Still further, this invention is to provide a process for producing the above pressed juice (green juice) of true grasses or its dry powder of true grasses, which comprises contacting the pressed juice of green leaves of true grasses with an anion exchange resin to separate and remove free chlorine and nitrate ions at least partially from the pressed juice, and optionally drying the resulting pressed juice (green juice) with said ions removed at least partially.

This invention will be described in more detail below.

Examples of the true grasses as a starting material to produce a green juice or its dry powder [hereinafter genetically termed a "green juice (powder)"] of this invention are barley, wheat, rye, oat and Italian rye grass. It is suitable to use green leaves of, among others, cereals, especially, young leaves of barley and oat, more exactly, green leaves before the maturity stage, preferably during or before the full heading stage, more preferably during or before the heading initiation stage, most preferably during the division initiating stage or before the heading initiation stage.

It is desirous to treat these tree grasses while they are as fresh as possible; in case of stored grasses, it is advisable to use grasses which have been subjected to means of preventing discoloration and degradation, such as inert gas storage, low-temperature storage, reduced pressure dehydration storage, and treatment with a sulfurous acid gas or a sulfurous acid salt. The starting plant is well washed to drop off adhering matters, sterilized with a germicide such as hyposulfurous acid as required, further washed well with water, and optionally sliced to a suitable size. In slicing, it may be dipped in a dilute sodium chloride aqueous solution (e.g., a 0.1-2.0% sodium chloride aqueous solution) and drained. Moreover, in any stage of the pretreatment, blanching may be conducted at a temperature of 100° to 140° C. under normal pressure (under reduced pressure or increased pressure as required), followed by quenching. This treatment can inactivate enzymes (e.g., chlorophilase, peroxidase and polyphenol oxidase) that can cause inconvenient discoloration, degradation, etc. of green leaves of true grasses.

After properly adding water, the green leaves of the thus pretreated true grasses are pressed into a juice. The pressing can easily be conducted by a combination of a mechanical crushing means such as a mixer, a juicer, or the like and a solid-liquid separation means such as centrifugal separation, filtration, or the like. In addition, a product obtained by redissolving in water a green juice powder of true grasses prepared in advance in a usual manner and properly filtering the solution can also be used as a starting material.

The thus obtained pressed juice of green leaves of true grasses is then subjected to separation and removal of free chlorine and nitrate ions ($Cl^-$ and $NO_3^-$). By this removal treatment, the other free inorganic anions, i.e., a sulfate ion ($SO_4^{2-}$), nitrite ion ($NO_2^-$), a phosphate ion ($PO_4^{3-}$), a silicate ion ($SiO_3^{2-}$), etc. are partially removed as components contained in small amounts in the green leaves of the true grasses. The inorganic anions composed mainly of chlorine and nitrate ions freely present in the green juice of the true grasses are hereinafter called "inorganic free anions".

Thus, the green juice becomes alkaline by the separation and removal of the inorganic free anions from the green juice, and pH of the green juice can be shifted nearly to pH of neutrality and weak alkalinity by properly adding a solution of an organic acid such as citric acid, tartaric acid, malic acid, ascorbic acid, lactic acid, or the like.

The separation and removal of these inorganic free anions composed mainly of chlorine and nitrate ions from the pressed juice can be carried out, for example, by absorption using an adsorbent that selectively adsorbs inorganic anions, dialyzation using a permselective membrane or a reverse osmosis membrane that selectively permeates the inorganic anions, or the like. Generally, electrodialysis using an ion exchange membrane and ion exchange treatment using an ion exchange resin are relatively simple, efficient and convenient.

Thus, the separation and removal of the inorganic free anions from the pressed juice can be carried out by charging the pressed juice into a cathode chamber of an electrolytic cell or an electrodialyzer having the cathode chamber and an anode chamber partitioned by an anion exchange membrane, charging water optionally containing an electrolyte into the anode chamber, and exerting a suitable voltage between the cathode and the anode. As the anion exchange membrane, an anion exchange membrane known per se is available which is often used in diaphragm electrolysis. Examples thereof are Selemion AMV, ASV and DMV [products of Asahi Glass Co., Ltd.], Aciplex [a product of Asahi Chemical Industry Co., Ltd.], and Neosepta [a product of Tokuyama Soda Coo., Ltd.].

The operating conditions of the above electrolytic cell or the electrodialyzer can vary depending on types of starting true grasses, scale of the electrolytic cell or the electrodialyzer, and the like. It is generally convenient to conduct the operation by keeping a constant voltage within the range of not exceeding a limit current value of an anion exchange membrane used and applying the maximum initial current value under such a condition. Concretely, a constant voltage within the range of 0.5 to 200 V is available and approximately 0.5 to 20 A can be used as the initial current value.

The temperature of operating the electrolytic cell or the electrodialyzer is usually about 0° C. to about 50° C., preferably about 2° C. to about 30° C.

The electrolysis or the electrodialysis can usually be carried out until the total amount of chlorine (Cl) and nitrate group ($NO_3$) of the pressed juice charged in the cathode chamber becomes not more than 9% by weight, preferably not more than 7% by weight based on the solids content. The amount of chlorine of the pressed juice can be determined by Mohr's method [compiled by Nihon Kagaku Kai, "New Experimental Chemistry Course - 9 - Analytical Chemistry [1]", p. 243, 1976, Marusen K.K.], and the amount of the nitrate group by Griess' method [D. F. Bolz, et al., ed., "Colorimetric Determination of Nonmetals", 2nd ed., p. 216 (1978), John Wiley] or a method of determination by sodium salicylate [compiled by Nihon Yakugaku Kai, "Hygiene Test Method—Commentary", 1990, p. 79, Kanehara Shuppan K.K.].

The electrolysis or the electrodialysis can be effected either batchwise or while continuously passing the pressed juice through the cathode chamber at a given flow rate.

The separation and removal of the inorganic free anions from the pressed juice can also be performed by contact with an anion exchange resin. Any anion exchange resin will do if having adsorbability to the above inorganic anions, and it may take any form and be particulate, filmy, fibrous, etc. Examples of the anion exchange resin are Amberlite IRA-68, Amberlite IRA-400, Amberlite IRA-410, Amberlite IRA-35, Amberlite IRA-45 (products of Organo K.K.), Dowex MSA-1, Dowex SBR-P, Dowex 66 (products of The Dow Chemical), Diaion SA10A and Diaion PA306 (products of Mitsubishi Chemical Industries, Ltd.).

The pressed juice and such an anion exchange resin can be contacted by, as in the usual ion exchange treatment, employing e.g. a method in which a sufficient amount of an ion exchange resin is added to the pressed juice and they are contacted while properly stirring them, a method in which the pressed juice is passed through a column filled with the anion exchange resin, a method in which the anion exchange resin is filled in a vessel having through-holes in which the resin is not leaked and dipped in the pressed juice, or the like. The contact between the pressed juice and the anion exchange resin can be carried out as above until the total amount of chlorine (Cl) and nitrate ($NO_3$) of the pressed juice becomes not more than 9% by weight, preferably not more than 7% by weight based on the solids content.

If the inorganic anions cannot thoroughly be separated and removed by one contact procedure, it is advisable to repeat the procedure twice or more by replacing the anion exchange resin.

The thus obtained green juice becomes strongly alkaline as a result of separating and removing the inorganic free anions. Accordingly, if pH of the green juice exceeds 9.5, it is advisable to adjust pH of the green juice to 6.3 to 9.5, preferably 6.5 to 8.5, more preferably 6.7 to 7.5 with the addition of an organic acid. Even when pH of the obtained green juice is less than 9.5, pH of the green juice can optionally be adjusted to the above preferable range with the addition of the organic acid, etc., thereby making it possible to obtain a stabler tasty green juice (powder).

Examples of the organic acid that can be used to adjust pH are citric acid, tartaric acid, malic acid, ascorbic acid, lactic acid, gluconic acid, and acetic acid.

It is possible to further remove inorganic free cations present in the green juice, especially, calcium and sodium ions from the green juice with the inorganic free anions separated and removed as aforesaid.

The green juice (powder) product can thereby be obtained which is more improved in shelf stability, and bitter and salty tastes. Besides, decrease in contents of potassium and sodium can provide the green juice (powder) product that e.g. patients who suffer from kidney disease and dislike the presence of these elements can take in without anxiety.

The separation and removal of the inorganic free cations can be carried out by, for example, (1) a method in which the green juice with the inorganic free anions separated and removed is introduced into an anode chamber of an electrolytic cell or an electrodialyzer having a cathode chamber and the anode chamber partitioned by a cation exchange membrane and water optionally containing an electrolyte into the cathode chamber respectively, and conducting electrolysis under the same electrolysis conditions as above; or (2) a method in which the green juice is contacted with a cation exchange resin as above.

Examples of the cathion exchange membrane available in the method (1) are Selemion, CMV (a product of Asahi Glass Co., Ltd.), Nafion (a product of du Pont), Flemion (a product of Asahi Glass Co., Ltd.), Aciplex (a product of Asahi Chemical Industry Co., Ltd.), and Neosepta (a product of Tokuyama Soda Co., Ltd.).

As the cation exchange resin that can be used in the contact treatment (2), any resin will do if having adsorbability to various inorganic free cations present in the green juice, especially, potassium and sodium ions. Examples thereof are Amberlite IRC-50, Amberlite IR-120B, Amberlite 200C, Amberlite 200CT, Amberlite 252, Amberlite IRC-84, Amberlite IRC-718 (products of Organo K.K.) Dowex 50W, Dowex 88 (products of The Dow Chemical), Diaion PK208, Diaion WK10 and Diaion 216 (products of Mitsubishi Chemical Industries, Ltd.).

Moreover, the inorganic free anions and the inorganic free cations may be separated and removed from the pressed juice at one stage. The method thereof is, for example, a method in which the pressed juice is introduced into a central chamber of an electrolytic cell or an electrodialyzer having a cathode chamber, the central chamber and an anode chamber partitioned by an anion exchange membrane mounted near an anode and a cation exchange membrane mounted near a cathode and water optionally containing an electrolyte into the cathode chamber and the anode chamber, and electrolysis is carried out by passing an electric current as above, a method in which the pressed juice is contacted with the anion exchange resin and the cation exchange resin simultaneously, or the like.

The extent of removing the inorganic free cations from the pressed juice is not particularly limited. It is, however, convenient that the removal is conducted until the total amount of potassium and sodium becomes usually not more than 10% by weight, preferably not more than 8% by weight based on the solids content of the pressed juice.

The amounts of potassium and sodium of the pressed juice (green juice) are determined by a HITACHI 170-30 model atomic-absorption/flame spectrophotometer after preparing a sample in a usual manner.

It is advisable that pH of the obtained green juice is 6.3 to 9.5, preferably 6.5 to 8.5, more preferably 6.7 to 7.5. When pH of the obtained green juice is not within the above range, pH may be adjusted by properly adding the above organic acid; an alkali such as a carbonate, a bicarbonate or a hydoxide of an alkaline earth metal, for example, ammonium hydroxide, calcium hydroxide, calcium carbonate, magnesium hydroxide, an alkaline solution accumulated in a cathode cell of an electrolytic cell, a glutamate such as calcium glutamate, or the like.

The green juice with the inorganic free anions and optionally the inorganic free cations removed as above may be used as such in beverages, food, quasi-drugs, drug raw materials, industrial raw materials, food preservative raw materials, chemical raw materials for cultivation of plants, etc. Preferably, the green juice is dried to form a solid powder.

Thus, the green juice may be subjected as such to a drying step. It can also be blended with an excipient and other auxiliary ingredients either before the drying step or before pH adjustment if required. Examples of the auxiliary ingredients that can be blended are as follows.

(1) Dry powders (including those which have previously been aged with a dilute acid and then dried) of plant fibrous materials such as a residue of a fibrous material formed after pressing the aforesaid green plant, a fruit juice residue, a sugar cane pressed juice residue, a vegetable pressed juice residue, etc., or water-soluble polysaccharides or mucosaccharides obtained by decomposing these plant fibrous materials with a decomposition enzyme such as cellulase, or the like.

(2) Lignin sulfonic acid obtained by decomposing wood chips, pulps, saw dusts, chaffs, defatted embryo buds, etc. with sodium sulfite or an alkaline substance (e.g., sodium hydroxide) to be water-soluble, and its salts.

(3) Products obtained by dissolving bones or cartilages of animals, fishes, etc., chondroitin sulfuric acid, heparin, etc. and extracting same with water.

(4) Fat-containing emulsion composed mainly of protein, milk, soybean milk, dry milk, skim milk, etc. or emulsion obtained by properly blending same with fats.

(5) Phosphates or polyphosphates such as ammonium phosphate, diammonium phosphate, potassium phosphate, dipotassium phosphate, and tripotassium phosphate; preferably sodium phosphate, disodium phosphate, trisodium phosphate, sodium polyphosphate, sodium metaphosphate, sodium pyrophosphate, potassium polyphosphate, potassium metaphosphate and potassium pyrophosphate.

(6) Nutrients such as ascorbic acid, biotin, calcium pantothenate, carotene, chlorinated choline, magnesium oxide, niacin, chlorinated pyridoxine, riboflavin, sodium pantothenate, thiamine hydrochloride, tocopherol, vitamin A, vitamin $B_{12}$, vitamin $D_2$, and the like;

masking agents such as sodium metaphosphate, sodium phosphate (primary, secondary, tertiary salts), sodium pyrophosphate, sodium tripolyphosphate, and the like; thickeners such as gum arabic, tragacanth, sodium alginate, methyl cellulose, carboxymethyl cellulose, potassium alginate, and the like; solidification inhibitors such as aluminum calcium silicate, calcium silicate, and the like; and preservatives such as sorbic calcium, benzoic acid, methyl p-hydroxybenzoate, sodium benzoate, and the like.

(7) Others: mannitol, sorbitol, lactic acid, soluble starch, dextrose, fructose, dextrin, cyclodextrin, polydextrin, and the like.

The pressed juice of green grasses treated in accordance with this invention is instantaneously heat-treated at any stage after its production but before the drying to decompose or inactivate inconvenient enzymes taking part in discoloration or degradation and also to sterilize bacteria that may be incorporated therein. This treatment can be conducted under normal pressure, reduced pressure or increased pressure. For example, treating conditions such as a temperature of 90° to 150° C. and a time of about 180 to 2 seconds, preferably a temperature of 80° to 100° C. and a time of 2 to 60 seconds can be employed. After this treatment, the temperature is rapidly lowered, especially below 10° C.

The green juice of the true grasses obtained as above is spray-dried or lyophilized as soon as possible, spray-drying being preferable. Spray-drying or liophilizing can be carried out in a manner known per se.

For example, spray-drying can be heat spray-drying with a hot air of about 120° to 200° C., preferably 140° to 170° C., or room temperature spray-drying in air dried with a suitable drying agent such as lithium chloride. In lyophilization, a temperature of a dry plate of 40° to 50° C. and a degree of vacuum of about 1.0 to 0.01 mm Hg are ordinarily employed.

The concentration of the green juice subjected to the drying step is within the range of about 1.5 to 30%. The higher concentration is better. To this end, a continuous thin film concentrating device, a vacuum concentrating device, etc. can be utilized in the concentration. In producing the green juice in this invention, it is possible to prevent discoloration and degradation during transportation, storage, etc. of the pressured juice (green juice) until it is subjected to the drying step, by a procedure such as replacing air with an inert gas, e.g., nitrogen, argon, etc. as required, or sealing an oxygen absorber such as glucose oxidase, or keeping a cold temperature, or shielding light; these steps are conducted either singly or in combination.

The green juice powder (green leaf powder) provided by this invention shows a vivid green color. Preferably, pH thereof is within 6.5 to 8 in a 1% aqueous solution, a dry weight loss is 5% or less, an ash content is 10 to 30%, and a crude protein content can be 10 to 20%, retaining a smell and a taste peculiar to the true grasses.

Thus, the green juice (powder) of this invention can be directly drunk as a food by blending it with water, hot water, plain soda, cider, milk or other beverages. Said juice can also be used as a food additive by blending it with various foodstuffs. Moreover, the green juice (powder) of this invention contains essential fatty acids and other phamaceutical substances in addition to vitamins, proteins, sugars derived from starting plants, and can effectively be utilized in the field of medicines too.

The green juice (powder) of this invention can properly be blended with salts, sugars, honey, dextrose and other seasonings or spices. It may also contain vitamins; an antioxidant such as d-isoascorbic acid, 1-ascorbic acid, propyl gallate, butyl hydroxyanisole or butyl hydroxy toluene; a food antiseptic such as dihydroacetic acid, sodium dihydroacetate, benzoic acid, or sodium benzoate; and an emulsifying agent such as a sucrose fatty acid ester or a sorbitan fatty acid ester. The green juice powder of this invention can take a shape of granules, pellets, coating tablets, capsules, or the like.

This invention is illustrated more specifically by the following Examples.

EXAMPLE 1

Young green leaves (100 kg) of barley before the heading initiation stage were washed with water, sterilized, further washed with water, crushed with a crusher, pressed with a juicer to obtain about 100 liters of the pressed juice of barley young leaves.

Using the pressed juice (pH 6.2) of the barley green leaves, free anions of the pressed juice were removed by electrodialysis with an anion exchange membrane as described below.

Selemion AMV [an anion exchange membrane of Asahi Glass Co., Ltd.] was mounted in a CS-O model laboratory electrodialyzer [manufactured by Asahi Glass Co., Ltd.]. Three liters of the green juice was charged on a cathode side, and a 2% sodium sulfate solution was charged on an anode side. A DC current with an initial current value of 5.2 A was applied with a constant voltage of 6 V to conduct electrolysis. As the electrolysis advanced, the amount of free chlorine ions contained in the green juice was reduced from 4.3% to 3.4%, and the amount of free nitrate ions from 4.8% to 3.8%, respectively. Since pH of the green juice on the cathode side was increased by this procedure, pH of the green juice was continuously adjusted to about 7.0 to 7.2 with a 10% citric acid solution, and withdrawn outside the system.

To the obtained green juice was added dextrin in an amount of twice the solids content of the green juice. Spray-drying was conducted at a blowing temperature of 180° C. and a discharge temperature of 120° C. to obtain 10.7 kg, per 100 liters of the starting green juice, of a spray-dried powder of the green juice of the barley young leaves in a yield of 90%.

The spray-dried powder of the green juice obtained by the above process was a product having excellent shelf stability, showing a vivid green color and having good taste and flavor.

EXAMPLE 2

A pressed juice of barley young leaves produced as in Example 1 was used as a starting material, and electrodialysis was conducted as described below to partially remove free anions and cations of the pressed juice.

Selemion CMV [a cation exchange membrane of Asahi Glass Co., Ltd.] was mounted on a cathode side of a CS-O model laboratory electrodialyzer [manufactured by Asahi Glass Co., Ltd.], and Selemion AMV [an anion exchange membrane of Asahi Glass Co., Ltd.] was mounted on an anode side thereof respectively. Three liters of the pressed juice of the barley young leaves were charged in a middle vessel between the anion and cation exchange membranes. A dilute citric acid solution was charged on the cathode side to suppress extreme increase in pH, and a 2% sodium sulfate solution was charged on the anode side. A DC current having an initial current value of 3.4 A was applied with a constant voltage of 6V, and electrolysis was conducted while circulating a dialyzate.

The green juice was continuously taken out from the middle vessel, and an alkaline solution on the cathode side was continuously added to adjust pH to 7.1 to 7.2. The electrodialysis could reduce the amount of free chlorine ions contained in the green juice from 3.8% to 2.7%, the amount of free nitrate ions from 4.5% to 3.8%, the amount of sodium ions from 1.1% to 0.7%, and the amount of potassium ions from 11.2% to 7.2%, respectively. To the green juice was added dextrin in an amount of twice the solids content of the green juice. Spray-drying was conducted at a blowing temperature of 190° C. and a discharge temperature of 120° C. to obtain 9.5 kg, per 100 liters of the starting green juice, of the green juice powder of the barley young leaves. Moreover, this product was quite stable in long-term storage.

EXAMPLE 3

Five liters of Amberlite IRA-68 were added to 100 liters of a pressed juice (pH 6.2) of barley young leaves obtained as in Example 1, and they were stirred at room temperature for 5 minutes. Subsequently, the ion exchange resin was removed, and the reduced amounts of the free chlorine ions and nitrate ions were measured. Consequently, the amount of the chlorine ions was reduced from 4.1% to 3.2%, and the amount of the nitrate ions from 4.3% to 3.5%, respectively. By this procedure, pH of the green juice was shifted to alkalinity. Therefore, pH of the pressed juice was adjusted to 7.2 with the addition of a 10% citric acid solution.

To the pressed juice was added dextrin in an amount of twice the solids content of the pressed juice. Spray-drying was carried out at a blowing temperature of 190° C. and a discharge temperature of 120° C. to obtain 10 kg of barley green leaf powder.

The barley green juice powder was a product showing a vivid green color and having good taste and flavor. Moreover, said product was quite stable in long-term storage.

EXAMPLE 4

Five liters of Amberlite IRA-35 were added to 100 liters of the pressed juice (pH 6.3) of barley young leaves obtained as in Example 1, and they were stirred at room temperature for 10 minutes. Then, 5 liters of Amberlite IRC-50 were added, and the mixture was stirred at room temperature for 5 minutes to remove cations. The amount of the chlorine ions was reduced from 3.7% to 2.5%, the amount of the nitrate ions from 4.5% to 3.2, the amount of the sodium ions from 1.2% to 0.72%, and the amount of the potassium ions from 9.3% to 6.9%, respectively. The ion exchange resin was removed, and pH was measured and found to be 7.5. The pH of the pressed juice was adjusted to 7.2 with the addition of a 10% citric acid aqueous solution.

To the pressed juice with pH adjusted as above was added dextrin in an amount of twice the solids content of the pressed juice. Spray-drying was conducted at a blowing temperature of 190° C. and a discharge temperature of 120° C. to obtain 9.5 kg of the barley green juice powder.

The barley green juice powder showed a vivid green color, had good taste and flavor, and was quite stable in long-term storage.

EXAMPLE 5

Five liters of Amberlite IRA-68 were added to 100 liters of a pressed juice (pH 6.2) of barley young leaves obtained as in Example 1, and they were stirred at room temperature for 5 minutes, followed by removing the ion exchange resin. To the thus treated pressed juice were added 5 liters of Amberlite IRC-50, and they were stirred at room temperature for 5 minutes. Then, the ion exchange resin was removed. This treatment reduced the amount of the chlorine ions from 3.2% to 2.7%, the amount of the nitrate ions from 4.3% to 3.2%, the amount of the sodium ions from 0.9% to 0.5%, and the amount of the potassium ions from 10.8% to 7.2%, respectively.

To the resulting pressed juice was added dextrin in an amount of twice the solids content of the pressed juice, and spray-drying was conducted at a blowing temperature of 190° C. and a discharge temperature of 120° C. to obtain 9.3 kg of a barley green juice powder.

The barley green juice powder showed a vivid green color, had good taste and flavor, and was quite stable in long-term storage.

EXAMPLE 6

Five liters of Diaion SA10A were added to 100 liters of a pressed juice (pH 6.3) of barley young leaves prepared as in Example 1 to remove anions. As a result, the amount of the chlorine ions in the green juice was reduced from 4.3% to 3.2%, and the amount of the nitrate ions from 4.8% to 3.5%, respectively. The pH of the green juice was adjusted to 7.3 with the addition of a 10% citric acid solution, and dextran in an amount of twice the solids content of the green juice were added. Spray-drying was carried out at a blowing temperature of 190° C. and a discharge temperature of 120° C. to obtain 9.6 kg of a green juice powder showing a vivid green color and having good taste and flavor. This product was quite stable in long-term storage.

EXAMPLE 7

Example 5 was repeated except that Amberlite IR-120B was used as a cation exchange resin. Consequently, the amount of the chlorine ions was reduced from 3.7% to 2.5%, the amount of the nitrate ions from 4.5% to 3.4%, the amount of the sodium ions from 1.2% to 0.7%, and the amount of the potassium ions from 9.5% to 6.5%, respectively. Spray-drying was conducted under the same conditions as in Example 5 to provide 9.5 kg of a green juice powder showing a vivid green color, having good taste and flavor and stable in long-term storage.

We claim:

1. A pressed juice or its dry powder of green leaves of barley or wheat which shows a vivid green color, the pressed juice having a pH in the range of 6.3 to 9.5, wherein the total content of chlorine and nitrate groups is not more than 7% by weight based on the solids content and the total content of potassium and sodium is not more than 8% by weight based on the solid content.

* * * * *